United States Patent
Alagy et al.

[19]

[11] Patent Number: 5,969,206
[45] Date of Patent: *Oct. 19, 1999

[54] REVERSE EMULSION ALIPHATIC ALKYLATION PROCESS WITH CATALYST-OLEFIN PREMIXING

[75] Inventors: Jacques Alagy, Charbonnieres; Jean-Francois Joly, Lyons; Eric Benazzi, Montesson; Jean-Charles Viltard, Valence, all of France; Luis Borges, Rio de Janerio, Brazil; Alain Forestiere, Vernaison, France

[73] Assignee: Institut Francais du Petrole, France

[*] Notice: This patent issued on a continued prosecution application filed under 37 CFR 1.53(d), and is subject to the twenty year patent term provisions of 35 U.S.C. 154(a)(2).

[21] Appl. No.: 08/785,041

[22] Filed: Jan. 17, 1997

Related U.S. Application Data

[63] Continuation of application No. 08/675,910, Jul. 5, 1996, abandoned.

[30] Foreign Application Priority Data

Jul. 6, 1995 [FR] France .................................. 95 08294

[51] Int. Cl.[6] ...................................................... C07C 2/58
[52] U.S. Cl. ............................ 585/723; 585/730; 585/731
[58] Field of Search .................................... 585/723, 730, 585/731

[56] References Cited

U.S. PATENT DOCUMENTS

| | | | |
|---|---|---|---|
| 3,686,354 | 8/1972 | Hervert ............................... | 260/683.43 |
| 4,041,100 | 8/1977 | Behrmann et al. ................ | 260/683.47 |
| 4,071,576 | 1/1978 | Behrmann ......................... | 260/638.47 |
| 4,371,731 | 2/1983 | Washer .................................. | 585/716 |

*Primary Examiner*—Glenn Caldarola
*Assistant Examiner*—Thuan D. Dang
*Attorney, Agent, or Firm*—Miller, White, Zelano, & Branigan, P.C.

[57] ABSTRACT

The invention concerns a process for the alkylation of at least one isoaffin selected from the group formed by isobutane and isopentane by at least one olefin containing 2 to 6 carbon atoms per molecule in the presence of a liquid acid catalyst, the process comprising mixing a feed comprising the olefin to be converted with an effluent comprising a major portion of isoparaffin in a first mixing zone, and forming an emulsion of said catalyst in a hydrocarbon effluent comprising a major portion of isoparaffin in an emulsifying zone, said effluent constituting the continuous phase of the emulsion thus formed, then mixing a major portion of the emulsion of acid in hydrocarbon effluent with a major portion of the diluted feed comprising the olefin in a second mixing zone, followed by carrying out the majority of the reaction in a reaction zone which is supplied by the major portion of said mixture.

14 Claims, 1 Drawing Sheet

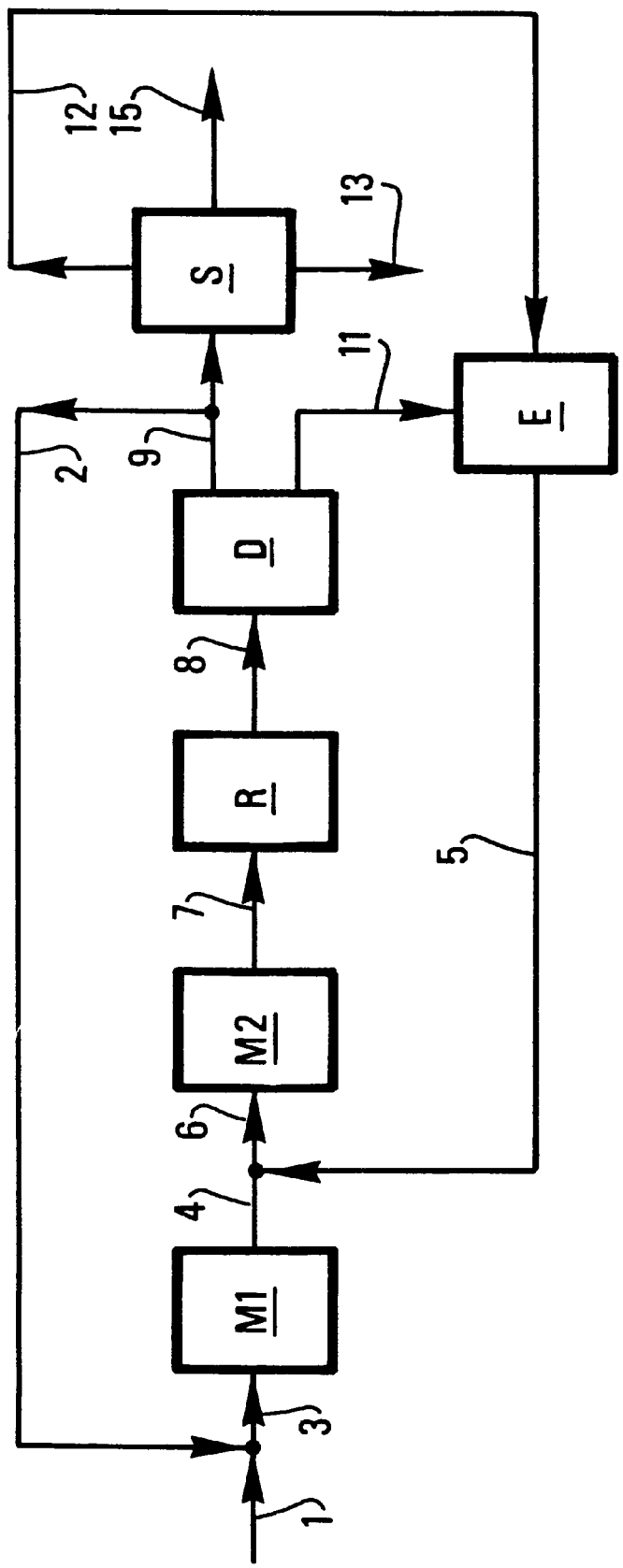

//5,969,206

REVERSE EMULSION ALIPHATIC ALKYLATION PROCESS WITH CATALYST-OLEFIN PREMIXING

CROSS REFERENCE TO RELATED APPLICATION

This application is a continuation of U.S. application Ser. No. 08/675,910 filed Jul. 5, 1996, now abandoned except for the addition of an inventor who was inadvertently omitted.

BACKGROUND OF THE INVENTION

The present invention concerns a catalytic alkylation process for at least one isoparaffin selected from the group formed by isobutane and isopentane by at least one olefin containing 2 to 6, preferably 3 to 6, carbon atoms per molecule, in the presence of at least one liquid acid catalyst.

The alkylation of an isoparaffin (isobutane and/or isopentane) by at least one olefin containing 2 to 6, preferably 3 to 6, carbon atoms per molecule can produce highly branched paraffinic hydrocarbons (for example from the group constituted by dimethylbutanes, trimethylpentanes, trimethylhexanes and trimethylheptanes), which are essential constituents of high octane number fuels. This alkylation reaction, termed aliphatic alkylation, requires the use of highly acidic catalysts primarily to reduce side reactions such as hydride abstraction from the olefin and polymerisation which produce less highly branched hydrocarbons with low octane numbers and unsaturated hydrocarbons, also cracking reactions and dismutation reactions.

A large number of liquid and solid acid catalysts are known for aliphatic alkylation of isoparaffins such as isobutane or isopentane, by at least one olefin such as propylene, 1- and 2-butenes, or isobutene. Currently, the most frequently used catalysts in the industry are liquid catalysts, namely concentrated sulphuric acid and hydrofluoric acid, used alone or as a mixture with Lewis acids such as boron trifluoride.

The majority of conventional processes are characterized in that the acid phase constitutes the continuous phase of the acid-hydrocarbon emulsion formed in the reactor.

The volume ratio of acid to hydrocarbons (mixture of isoparaffins and olefins) is thus greater than one. Further, the emulsion is generally formed in the alkylation reactor itself, i.e., in the presence of the feed to be converted which contains the olefin (see, for example, the use of Stratco technology employing liquid sulphuric acid: L. F. Albright, Chem. Eng., Aug. 15, 1966, p. 143 and L. F. Albright, Oil & Gas Journal, Nov. 12, 1990).

When the catalyst is sulphuric acid, the conventional isoparaffin alkylation process using a sulphuric acid catalyst has a number of disadvantages, among them: the impossibility of reaching temperatures of less than 0° C. in the reactor in the presence of more than 97% by weight strength sulphuric acid. The viscosity of sulphuric acid becomes too high at such temperatures and, since the acid is the continuous phase, it becomes impossible to stir the medium; the olefin in the feed and the acid recycled from the settler are injected directly into the reactor in immediate proximity to the moving part of the stirrer. Thus this latter must carry out two operations: create the acid-hydrocarbon emulsion and dilute the olefin in the hydrocarbon phase to limit local superconcentration of the olefin, which is not carried out sufficiently effectively; the residence time of the hydrocarbon phase in the settler is high, usually about one hour. Since the temperature in the settler is usually above about 15° C., some isoparaffins containing more than 5 carbon atoms per molecule undergo degradation reactions. Examples of these degradation reactions are oxidation of paraffins by sulphuric acid to produce water and $SO_2$. These reactions contribute to catalyst deactivation. Other reactions are uncontrolled decomposition of alkyl sulphates, in particular butyl sulphates. These decomposition reactions are the cause of the formation of unsaturated oligomers which deactivate the catalyst.

International patent application PCT WO 95/04.019 describes a process for the alkylation of an olefin by an isoparaffin in the presence of liquid sulphuric acid, the process comprising a zone for preparing an emulsion of acid in the isoparaffin followed by a reaction zone supplied with the emulsion into which the olefin is injected, the ratio by volume of sulphuric acid: hydrocarbons present in the reaction zone being in the range 0.3:1 to 0.5:1. Thus the continuous phase of the prepared emulsion in that process is the hydrocarbon phase. That patent application also describes means for forming the emulsion and adding the olefin to the reaction zone, as well as an apparatus for carrying out the process.

In International patent application PCT WO 95/04.019, the olefin is injected directly into the reaction zone. Thus in that zone, the olefin must be diluted in the hydrocarbon phase in such a manner as to limit local superconcentration of the olefin.

The alkylation of isobutane and/or isopentane comprises a first, very rapid, step of adsorption of the olefin on the acid catalyst to form a type of acid-olefin "complex", followed by reaction of the "complex" with isobutane and/or isopentane. If carried out under the temperature and pressure conditions used for the reaction, the first step can encourage the formation of polymers, which are undesirable secondary products, to the detriment of "complex" formation. This has a highly deleterious effect on the process yield. It is thus of advantage to mix the olefin and the catalyst in a zone preceding the reaction zone, under temperature and pressure conditions which are primarily favourable to formation of the "complex".

SUMMARY OF THE INVENTION

The process of the invention is thus a process for the alkylation of at least one isoparaffin selected from the group formed by isobutane and isopentane by at least one olefin containing 2 to 6, preferably 3 to 6, carbon atoms per molecule in the presence of a liquid acid catalyst, the process comprising mixing a feed comprising the olefin to be converted with an effluent comprising a major portion of isoparaffin in a first mixing zone to form a diluted feed comprising the olefin, and forming an emulsion of said catalyst in a hydrocarbon effluent comprising a major portion of isoparaffin in an emulsifying zone, said effluent constituting the continuous phase of the emulsion thus formed, then mixing a major portion of the emulsion of acid in hydrocarbon effluent with a major portion of the diluted feed comprising the olefin in a second mixing zone, followed by carrying out the majority of the reaction in a reaction zone which is supplied by the major portion of said mixture.

The first mixing operation and emulsion formation operation may or may not take place simultaneously, the order of the operations being of little importance when they are carried out successively.

In one preferred implementation of the process of the invention, the process further comprises passing a major portion of the effluent from the reaction zone to a settling zone to produce an effluent comprising a major portion of the liquid acid and a hydrocarbon phase comprising mainly the isoparaffin and alkylate. Then, in a first option, the process is preferably such that the catalyst supplied to the emulsifying zone comprises the major portion of the effluent comprising a major portion of the liquid acid leaving the settling zone. In a second option, which may or may not be independent of the preceding option, the major portion of the effluent comprising a major portion of isoparaffin entering the first mixing zone is formed by a portion of the hydrocarbon phase.

In the preferred implementation described above, and independently or otherwise of each of the options described above, the process can preferably further comprise a separation zone which produces a hydrocarbon effluent comprising a major portion of isoparaffin, and which produces an alkylate reaction product, the separation zone being supplied with a portion of the hydrocarbons phase obtained from the outlet to the settling zone. The process of the invention can then be such that the other portion of the hydrocarbon phase obtained from the outlet to the settling zone is comprised in the effluent comprising a major portion of isoparaffin entering the first mixing zone. A further possibility, which may or may not be independent of the preceding possibility, is that the process of the invention is such that a major portion of the hydrocarbon effluent comprising a major portion of isoparaffin which supplies the emulsifying zone consists of the hydrocarbon effluent comprising a major portion of isoparaffin leaving the separation zone.

Further, the process of the invention includes addition of an isoparaffin. This isoparaffin addition constitutes the isoparaffin supply to the process of the invention, which is carried out in accordance with the stoichiometry of the alkylation reaction with respect to the olefin. Preferably, the process of the invention is such that the isoparaffin is added by mixing the added isoparaffin with the feed comprising the olefin to be converted before the inlet of the feed to the first mixing zone. Thus, more preferably, the feed entering the first mixing zone mainly comprises the supply of olefin(s) and isoparaffin(s) to the process.

The process of the invention generally includes addition of fresh catalyst, i.e., catalyst which has not yet been subjected to any chemical reaction or a catalyst which has been subjected to a chemical reaction and regenerated in a regeneration zone to restore its initial catalytic properties. The process also comprises extraction of used catalyst. Preferably, the major portion of added fresh catalyst is from a regeneration zone.

The process of the invention is such that the liquid acid catalyst is generally selected from the group formed by sulphuric acid and hydrofluoric acid, and preferably the liquid acid catalyst is sulphuric acid, which itself preferably has a strength of over 96% by weight.

The liquid sulphuric acid used in the process of the invention in the reaction zone is at a temperature which is generally below 0° C. and has the advantage over 96% to 99% by weight strength sulphuric acid, which is used in current alkylation units (in conventional processes with a reaction zone operating at a temperature generally above 0° C.), of having an equal or higher acidity while at the same time being far less oxidising in nature, to obtain an alkylate with a higher octane number than that which is currently obtained using those conventional processes. The use of the catalyst in accordance with the invention thus leads to a reduction in catalyst consumption and hence to a reduction in the costs of the alkylation unit.

The process of the present invention is applicable to any liquid acid catalyst, such as a catalyst comprising at least one acid selected from the group formed by sulphuric acid and hydrofluoric acid, to which at least one additive has been added, such as $HB(HSO_4)_4$.

As an example, a catalyst used in accordance with the process of the present invention comprises (in weight %), 0.4 to 68.8%, preferably 0.4 to 60%, of $HB(HSO_4)_4$, and 31.2% to 99.6%, preferably 40% to 99.6%, of $H_2SO_4$, the catalyst being such that it contains no unassociated sulphur trioxide ($SO_3$), i.e., has not reacted with boric acid but which may contain boric acid, in excess and unassociated, i.e., not reacted with sulphur trioxide.

The process of the present invention, more particularly in its preferred implementation which comprises passing a major portion of the effluent from the reaction zone to a settling zone, has a number of advantages over known alkylation processes of the prior art, among them:

- using a lower temperature, in particular below 0° C.;
- obtaining higher settling rate than those obtained when the acid phase is the continuous phase of the emulsion;
- using a very low temperature for mixing the olefin with the liquid acid catalyst, notably a temperature which is lower than the temperature of the reaction zone, in particular below 0° C.;
- carrying out the settling operation at a low temperature, which advantage adds to that of being able to employ a short residence time in the settling zone, thus considerably limiting the incidence of secondary reactions which occur in the settlers in conventional processes.

Thus a preferred implementation of the process of the invention concerns an alkylation process in which a feed comprising at least one isoparaffin selected from the group formed by isobutane and isopentane, preferably isobutane, and at least one olefin containing 2 to 6, preferably 3 to 6, carbon atoms per molecule, is treated in the presence of a liquid acid catalyst, the process comprising the following steps:

1. In a zone (E), emulsifying a major portion of the liquid acid from a settling zone (D) described in step (5) and a major portion of a hydrocarbon effluent comprising a major portion of the isoparaffin from an isoparaffin-alkylate separation zone (S) described in step (6), said major portion of said effluent constituting the continuous phase of the emulsion. The effluent from zone (E) is an emulsion of acid in a liquid hydrocarbon effluent comprising a major portion of the isoparaffin. This emulsion is constituted by fine droplets of acid dispersed in a continuous hydrocarbon phase.
2. In a first mixing zone (M1), mixing a feed and a portion of the hydrocarbon phase comprising mainly the isoparaffin and alkylate leaving settling zone (D) described in step (5), to obtain a diluted feed. Steps (1) and (2) are at least partially carried out simultaneously or successively, in which latter case the order in which the steps are carried out is of no great importance.
3. In a second mixing zone (M2), mixing the diluted feed described in step (2) with the emulsion described in step (1), to obtain a mixture of acid in a liquid hydrocarbon effluent which is the continuous phase of the emulsion.
4. Carrying out the major portion of the alkylation reaction in a zone (R), which zone (R) is supplied by the major portion of the mixture from zone (M2) described in step (3), preferably introduced to at least the inlet to zone (R). The flow rate of the effluent entering reaction zone (R) is selected so that throughout the zone, the emulsion remains constituted by droplets of acid dispersed in a continuous hydrocarbon phase.

5. Separating the major portion of the effluent leaving reaction zone (R) described in step (4) in a settling zone (D). The effluent is constituted by an emulsion of acid in a continuous hydrocarbon phase. The two phases, acid and hydrocarbon, are separated in settling zone (D). Settling zone (D) generally comprises at least one settler. The type of settler used is chosen so that the time required to carry out the settling operation is as short as possible, and so that the temperature of the acid phase in the settler remains below 0° C. Settling zone (D) produces an effluent comprising a major portion of liquid acid, the major portion of this effluent being recycled to emulsifying zone (E) described in step (1). It also produces a hydrocarbon phase mainly comprising the isoparaffin and alkylate, a portion of which is recycled to the first mixing zone (Ml) described in step (2).

6. Isoparaffin-alkylate separation of the other portion of the liquid hydrocarbon phase comprising mainly the isoparaffin and alkylate from settling zone (D) described in step (5) is carried out in a zone (S) to produce a hydrocarbon effluent comprising a major portion of isoparaffin, the major portion of which is recycled to zone (E) described in step (1). Optionally and preferably, a hydrocarbon effluent comprising a major portion of normal-paraffin is obtained as a purge, and a hydrocarbon effluent comprising a major portion of an alkylate is obtained as a product.

The operating conditions, in particular the temperature and pressure, of the process for the alkylation of isoparaffin(s) by at least one olefin of the present invention are selected so that the reaction medium is liquid.

When carrying out the process of the invention, mixing in zone (M1) and zone (M2) can be effected using various techniques which are known to the skilled person. As an example, at least one static in-line mixer (containing Sulzer packing, for example) can be used. In all cases, it is particularly advantageous to use static mixers upstream of reaction zone (R) to ensure the best possible contact between the different effluents before their introduction into reaction zone (R). The flow rate of the effluent entering reaction zone (R) is selected so that throughout the reaction zone (R), the emulsion is constituted by droplets of acid dispersed in a continuous hydrocarbon phase.

One or more reactors can be used to carry out the process of the invention.

In a preferred implementation of the process of the invention, the effluent comprising a major portion of the catalyst is extracted continuously or discontinuously from the bottom of settling zone (D) and fresh catalyst is introduced continuously or discontinuously to the inlet to emulsifying zone (E) to maintain constant the quality of alkylate produced.

The temperature in emulsifying zone (E) is generally in the range −20° C. to +10° C., preferably in the range −0° C. to +10° C., and the pressure is such that all the hydrocarbon present in said zone is liquid.

The temperature in second mixing zone (M2) is generally in the range −20° C. to +10° C., preferably in the range −15° C. to 0° C., and more preferably in the range −10° C.to −3° C., and the pressure is such that all the hydrocarbon present in said zone is liquid.

The temperature in the alkylation zone or reaction zone (R) is generally in the range −20° C. to +10° C., preferably in the range −10° C. to +5° C., and more preferably in the range −10° C. to 0° C. , and the pressure is such that all the hydrocarbon present in said zone is liquid.

The temperature in settling zone (D) is general in the range −20° C. to +10° C., preferably in the range −10° C. to +5° C., and more preferably in the range −10° C. to 0° C., and the pressure is such that all the hydrocarbon present in said zone is liquid.

The residence time for compounds in second mixing zone (M2) is very short, generally between 1 second and 2 minutes, preferably between 1 second and 1 minute, so that the alkylation reaction cannot occur to any great extent in zone (M2). Nevertheless, it is considered that only the major portion of the reaction occurs in zone (R).

The residence time for the effluent from reaction zone (R) in settling zone (D) is very short, shorter than in conventional alkylation reactions in which the continuous phase of the isoparaffin-acid emulsion is the acid. It is generally in the range 1 minute to 1 hour, preferably in the range 1 minute to 30 minutes, and more preferably in the range 1 minute to 15 minutes.

The residence time for the catalyst in emulsifying zone (E) is generally in the range 1 second to 20 minutes, preferably in the range 1 second to 10 minutes.

The residence time for compounds, more particularly the catalyst, in reaction zone (R) is generally in the range 1 minute to 1 hour, preferably in the range 1 minute to 30 minutes.

The ratio of the volume flow rates of effluent comprising a major portion of acid from the lower portion of settling zone (D) to the hydrocarbon effluent comprising a major portion of isoparaffin from the head of separation zone (S) at the inlet to emulsifying zone (E) is selected so that the proportion of acid in the emulsifying zone is in the range 5% to 49% by volume, preferably in the range 10% to 45% by volume, and more preferably in the range 30% to 45% by volume.

The proportion of acid in reaction zone (R) is in the range 20% to 49% by volume preferably in the range 30% to 45% by volume.

The feed is preferably dried over a molecular sieve and selectively hydrogenated before introducing it to first mixing zone (M1) to eliminate highly unsaturated compounds which could inhibit the catalytic phase.

In general, the hourly space velocity, expressed as the volume of olefin(s) introduced per unit volume of catalyst in zone (R) per hour, is in the range $0.1\ h^{-1}$ to $5\ h^{-1}$, preferably in the range $0.2\ h^{-1}$ to $2\ h^{-1}$.

In order to limit secondary degradation reactions of the $C_5$–$C_{12}$ isoparaffins present in the liquid effluent passing through reaction zone (R), the separation operation (zone (S)) is preferably carried out so that the ratio of the mass flow rates of the hydrocarbon effluent comprising a major portion of isoparaffin (for example isobutane) extracted overhead from separation zone (S) to the hydrocarbon effluent comprising a major portion of alkylate extracted from the bottom of zone (S) is in the range 5:1 to 100:1, preferably in the range 10:1 to 30:1.

The accompanying figure illustrates the invention, more precisely one of the preferred implementations of the process of the invention, without in any way limiting its scope.

The feed to be converted, constituted by a liquid phase mixture from line (1) comprising at least one isoparaffin and at least one olefin containing 2 to 6 carbon atoms per molecule, is mixed with an effluent from line (2), which is a mixture of isoparaffin and alkylate and the portion of the effluent (9) leaving settler (D) which is not sent to separation zone (S). Mixed lines (1)and (2) form line (3) which supplies static mixer (M1). After mixing with the effluent from line (5), the effluent leaving (M1) is injected into a second static mixer (M2). The effluent from line (5) is constituted by an emulsion of acid in isoparaffin, the isoparaffin originating overhead from a separation zone (S) via line (12) and the acid originating from the bottom of settling zone (D) via line (11). The effluent leaving mixer (M2), constituted by an emulsion in a continuous hydrocarbon phase, is introduced via line (7) into reaction zone (R). The effluent leaving reaction zone (R), i.e., the emulsion of acid in a continuous hydrocarbon phase mainly constituted by the isoparaffin and alkylate, is introduced into settling zone (D). Acid is extracted from the lower portion of zone (D) via line (11) and, after mixing with effluent (isoparaffin) from line (12), the acid is introduced to the inlet to zone (E), A hydrocarbon phase containing excess isoparaffin and the alkylate is extracted from the upper portion of settling zone (D) via line (9). A portion of this effluent is recycled via line (2) to the inlet to the first static mixer (M1) and the other portion is introduced to isoparaffin-normal paraffin-alkylate separation zone (S). The alkylate separated in zone (S) is extracted from the unit as a product via line (13). Normal paraffin is extracted in a side stream from zone (S) via line (15), as a purge. The isoparaffin-rich liquid fraction extracted overhead from zone (S) is recycled to the inlet to emulsifying zone (E) via line (12).

BRIEF DESCRIPTION OF THE DRAWING

The FIGURE is a schematic representation of an apparatus that performs a method of the present invention.

We claim:

1. A process for the alkylation of at least one isoparaffin selected from the group consisting of isobutane and isopentane with at least one olefin containing 2 to 6 carbon atoms per molecule in the presence of a liquid acid catalyst, said process comprising (1) mixing a feed comprising the olefin to be converted with a first effluent comprising (a) major portion of isoparaffin and (b) a minor portion of alkylate in a first mixing zone so as to obtain a diluted feed, (2) forming an emulsion of said liquid acid catalyst in a second hydrocarbon effluent depleted of said alkylate and comprising a major portion of isoparaffin, said second hydrocarbon effluent constituting the continuous phase of the emulsion thus formed, (3) mixing a major portion of the resultant emulsion of acid in the second hydrocarbon effluent with a major portion of the diluted feed comprising the olefin in a second mixing zone, (4) passing a third effluent from said second mixing zone to a reaction zone, and (5) conducting most of said alkylation reaction in said reaction zone to form said alkylate, wherein the temperature of the second mixing zone is less than the temperature of the reaction zone.

2. A process according to claim 1, further comprising passing a major portion of the effluent from the reaction zone to a settling zone to obtain an effluent comprising a major portion of the liquid acid and a hydrocarbon phase mainly comprising the isoparaffin and the alkylate.

3. A process according to claim 2, in which a major portion of the catalyst supplied to the emulsifying zone consists of the effluent comprising a major portion of the liquid acid leaving said settling zone.

4. A process according to claim 2, in which a major portion of the effluent comprising a major portion of isoparaffin entering the first mixing zone is constituted by a portion of said hydrocarbon phase.

5. A process according to claim 2, further comprising a separation zone which produces a hydrocarbon effluent comprising a major portion of isoparaffin, and which produces an alkylate as a reaction product, said separation zone being supplied with a portion of the hydrocarbon phase obtained from the outlet to the settling zone.

6. A process according to claim 5, in which a major portion of the hydrocarbon effluent comprising a major portion of isoparaffin which supplies the emulsifying zone consists of the hydrocarbon effluent comprising a major portion of isoparaffin leaving the separation zone.

7. A process according to claim 1, comprising addition of isoparaffin.

8. A process according to claim 1, comprising addition of fresh catalyst and extraction of used catalyst.

9. A process according to claim 1, in which said liquid acid catalyst is sulphuric acid.

10. A process according to claim 1, wherein the temperature of the second mixing zone is below 0° C.

11. A process according to claim 1, wherein the temperature of the second mixing zone is in the range −15° C. to 0° C. and the temperature of the reaction zone is in the range of −10° C. to 5° C.

12. A process for the alkylation of at least one isoparaffin selected from the group consisting of isobutane and isopentane with at least one olefin containing 2 to 6 carbon atoms per molecule in the presence of a liquid acid catalyst, said process comprising (1) mixing a feed comprising the olefin to be converted with a first effluent comprising (a) a major portion of isoparaffin and (b) a minor portion of alkylate in a first mixing zone so as to obtain a diluted feed, (2) forming an emulsion of said liquid acid catalyst in a second hydrocarbon effluent depleted of said alkylate and comprising a major portion of isoparaffin, said second hydrocarbon effluent constituting the continuous phase of the emulsion thus formed, (3) mixing a major portion of the resultant emulsion of acid in the second hydrocarbon effluent with a major portion of the diluted feed comprising the olefin in a second mixing zone, (4) passing a third effluent from said second mixing zone to a reaction zone, and (5) conducting most of said alkylation reaction in said reaction zone to form said alkylate, wherein the temperature of the second mixing zone is less than the temperature of the reaction zone, and wherein the residence time for compounds within the second mixing zone is between 1 second and two minutes.

13. A process for the alkylation of at least one isoparaffin selected from the group consisting of isobutane and isopentane with at least one olefin containing 2 to 6 carbon atoms per molecule in the presence of a liquid acid catalyst, said process comprising (1) mixing a feed comprising the olefin to be converted and at least one isoparaffin with a first effluent comprising (a) a major portion of isoparaffin and (b) a minor portion of alkylate in a first mixing zone so as to obtain a diluted feed, (2) forming an emulsion of said liquid acid catalyst in a second hydrocarbon effluent depleted of said alkylate and comprising a major portion of isoparaffin, said second hydrocarbon effluent constituting the continuous phase of the emulsion thus formed, (3) mixing a major portion of the resultant emulsion of acid in the second hydrocarbon effluent with a major portion of the diluted feed comprising the olefin in a second mixing zones (4) passing a third effluent from said second mixing zone to a reaction zone, and (5) conducting most of said alkylation reaction in said reaction zone to form said alkylate, wherein the temperature of the second mixing zone is less than the temperature of the reaction zone, wherein the temperature of the second mixing zone is below 0° C. and the residence time for compounds within the second mixing zone at a temperature less than 0° C. in between 1 second and two minutes.

14. A process for the alkylation of at least one isoparaffin selected from the group consisting of isobutane and isopentane with at least one olefin containing 2 to 6 carbon atoms per molecule in the presence of a liquid acid catalyst, said process comprising (1) mixing a feed comprising the olefin to be converted and at least one isoparaffin with a first effluent comprising (a) a major portion of isoparaffin and (b) a minor portion of alkylate in a first mixing zone so as to obtain a diluted feed, (2) forming an emulsion of said liquid acid catalyst in a second hydrocarbon effluent depleted of said alkylate and comprising a major portion of isoparaffin, said second hydrocarbon effluent constituting the continuous phase of the emulsion thus formed, (3) mixing a major portion of the resultant emulsion of acid in the second hydrocarbon effluent with a major portion of the diluted feed comprising the olefin in a second mixing zone, (4) passing a third effluent from said second mixing zone to a reaction zone, and (5) conducting most of said alkylation reaction in said reaction zone to form said alkylate, wherein the temperature of the second mixing zone is less than the temperature of the reaction zone.

\* \* \* \* \*